United States Patent
Jung et al.

(10) Patent No.: US 10,420,858 B2
(45) Date of Patent: Sep. 24, 2019

(54) CELL CARRIER FOR SKIN TISSUE REGENERATION CONTAINING CHITOOLIGOSACCHARIDE AND METHOD FOR PRODUCING THE SAME

(71) Applicant: PUKYONG NATIONAL UNIVERSITY INDUSTRY-UNIVERSITY COOPERATION FOUNDATION, Busan (KR)

(72) Inventors: Won-Kyo Jung, Busan (KR); Seok-Chun Ko, Jeju-si (KR); Gun-Woo Oh, Busan (KR)

(73) Assignee: Pukyong National University Industry-University Cooperation Foundation (KR)

( * ) Notice: Subject to any disclaimer, the term of this patent is extended or adjusted under 35 U.S.C. 154(b) by 0 days.

(21) Appl. No.: 15/754,508

(22) PCT Filed: Apr. 6, 2016

(86) PCT No.: PCT/KR2016/003553
§ 371 (c)(1),
(2) Date: Feb. 22, 2018

(87) PCT Pub. No.: WO2017/065368
PCT Pub. Date: Apr. 20, 2017

(65) Prior Publication Data
US 2018/0250436 A1 Sep. 6, 2018

(30) Foreign Application Priority Data
Oct. 16, 2015 (KR) .......................... 10-2015-0144988

(51) Int. Cl.
| A61L 27/20 | (2006.01) |
| A61L 27/24 | (2006.01) |
| C12N 11/04 | (2006.01) |
| C12N 11/06 | (2006.01) |
| A61L 27/36 | (2006.01) |
| A61L 27/26 | (2006.01) |
| A61L 27/60 | (2006.01) |

(52) U.S. Cl.
CPC .............. *A61L 27/20* (2013.01); *A61L 27/24* (2013.01); *A61L 27/26* (2013.01); *A61L 27/3604* (2013.01); *A61L 27/3687* (2013.01); *A61L 27/3691* (2013.01); *A61L 27/60* (2013.01); *C12N 11/04* (2013.01); *C12N 11/06* (2013.01); *A61L 2430/34* (2013.01); *A61L 2430/40* (2013.01)

(58) Field of Classification Search
CPC ...... A61L 27/24; A61L 27/26; A61L 27/3633; A61L 27/3645; A61L 27/3691; A61L 27/3666; A61L 27/3687
See application file for complete search history.

(56) References Cited

FOREIGN PATENT DOCUMENTS

| KR | 10-2007-0082114 A | 8/2007 |
| KR | 10-2009-0097582 A | 9/2009 |
| KR | 10-2013-0099356 A | 9/2013 |
| KR | 10-2013-0101204 A | 9/2013 |
| KR | 10-2013-0124797 A | 11/2013 |

OTHER PUBLICATIONS

Chandika et al (Fish collagen/alginate/chitooligosaccharides integrated scaffold for skin tissue regeneration application; International Journal of Biological Macromolecules, 81, 2015, p. 504-513). (Year: 2015).*
Venkatesan et al (Development of Alginate-Chitosan-Collagen Based Hydrogels for Tissue Engineering; Journal of Biomaterials and Tissue Engineering, vol. 5, 458-464, 2015) (Year: 2015).*
Choi et al (Bioactive fish collagen/polycaprolactone composite nanofibrous scaffolds fabricated by electrospinning for 3D cell culture; Journal of Biotechnology, 205, 47-58, 2015) (Year: 2015).*
Chandika, P. et al. "Fish Collagen/alginate/chitooligosaccharides Integrated Scaffold for Skin Tissue Regeneration Application." International Journal of Biological Macromolecules, Nov. 2015 (published online Aug. 22, 2015), vol. 81, pp. 504-513.
Chandika, P. "Development of Biologically and Mechanically Induced Sponge Scaffold Composed of Marine Fish Collagen/alginate/chitooligosaccharides for Skin Tissue Regeneration Application." Master's Thesis of Pukyong National University, Aug. 2015, pp. 1-65.
Chandika, P. et al. "Development and Characterization of Three Dimensional Scaffold from Marine Originated Collagen/alginate and Chitooligosaccharides for Skin Tissue Engineering Application." World Aquaculture Society Meetings 2015 Jeju, May 26-30, 2015, pp. 1-792. See p. 650.
Choi, Da Jeong et al. "Bioactive fish collagen/polycaprolactone composite nanofibrous scaffolds fabricated by electrospinning for 3D cell culture." Journal of Biotechnology, 2015, vol. 205, pp. 47-58.
Venkatesan, Jayachandran et al. "Development of Alginate-Chitosan-Collagen Based Hydrogels for Tissue Engineering." Journal of Biomaterials and Tissue Engineering, 2015, vol. 5, pp. 458-464.

* cited by examiner

*Primary Examiner* — Micah Paul Young
(74) *Attorney, Agent, or Firm* — JHK Law; Joseph Hyosuk Kim (57) ABSTRACT

Provided are a cell carrier for skin tissue regeneration using chitooligosaccharide and a method for producing the same. The cell carrier according to the present invention includes fish-derived collagen (FC), alginate (A), and chitooligosaccharide (COS1) of 1 to 3 kDa, and thus has excellent biocompatibility with dermal fibroblasts and has an excellent effect of being utilized as a cell carrier for skin tissue regeneration.

2 Claims, 9 Drawing Sheets

CELL CARRIER FOR SKIN TISSUE REGENERATION CONTAINING CHITOOLIGOSACCHARIDE AND METHOD FOR PRODUCING THE SAME

TECHNICAL FIELD

The present invention relates to a cell carrier for skin tissue regeneration including chitooligosaccharide and a method for preparing the same, and more particularly to a cell carrier for skin tissue regeneration including fish-derived collagen (Fish collagen, FC), alginate (A), and 1 to 3 kDa chitooligosaccharide (COS1), which are excellent in biocompatibility.

BACKGROUND ART

The development of science and the resulting increase in human life expectancy have led to increased problems of various diseases, aging, and organ damage due to various accidents, and thus there is a growing interest in the tissue-engineering to regenerate tissues.

A cell carrier (Scaffold) refers to a physical scaffold and adhesion substrate made possible for culture in vitro and implantation of tissue cells, and these cell carriers are used for cell transplantation for tissue regeneration. In the case of epithelial cells used for skin tissue regeneration, it is required to be used after incubation in the cell carrier because adhesion of the cells and accompanying transfer and proliferation are possible only when there is a contact area between the substrates.

Since such cell carrier for skin tissue regeneration is directly inserted into the body, collagen and the like, which are derived from terrestrial animals such as pigs and cattle, which are biodegradable, are currently used. However, the use of collagen derived from terrestrial animals has been avoided due to safety issues such as mad cow disease and foot-and-mouth disease, and interest in natural substances derived from safer marine organisms has been increasing.

The oceans are known to account for more than 70% of the surface area of the Earth's surface and to be the source of hundreds of thousands of species of biological materials, which account for 80% of whole animals in the Earth. Recently, marine natural substances obtained from marine include a large amount of various minerals and physiologically active materials and have proved that they have excellent biocompatibility compared to other animal natural products. Thus, in advanced countries, marine organisms are noticed as new substances for physiological activity and new materials for the tissue-engineering. Thus, in order to explore new natural materials and to create new added value, the biotechnology and bioorganic chemistry techniques are applied to the marine natural materials to concentrate on development of biomaterials In particular, chitin and chitosan in marine natural materials refer to natural cationic polysaccharides present in the cell walls of crustacean shells, insect epidermis, and some microorganisms. Chitosan, prepared by alkaline deacetylation of chitin, is composed of $\beta(1\rightarrow4)$-bond N-acetyl-D-glucosamine units and has a variety of biological activities. Chitooligosaccharide is hydrolyzed to chitosan derivatives. Unlike chitosan, chitooligosaccharide has free amino groups with a shorter chain length in the D-glucosamine unit. For such reason, it is known that chitooligosaccharide is soluble in natural aqueous solutions and thus can be easily applied to in vitro and in vivo systems and has anti-tumor, anti-fungal, antibacterial, anti-virus and reactive oxygen species (ROS) scavenging ability according to a range of their molecular weight (kDa). However, there is no hitherto-known method of utilizing chitooligosaccharide for cell carrier for skin tissue regeneration depending on a range of the molecular weight (kDa).

As a prior art of the present invention, a method for manufacturing a carrier of transplanting pancreatic islet cells using atelocollagen, and artificial pancreas manufactured by the same method is disclosed in Korea Patent Registration No. 10-1327630, but relates to a carrier of transplanting pancreatic islet cells in which alginate and atelocollagen derived from cationized pigs are used as constituents to increase the survival rate of islet cells and insulin secretion. Also, nanoparticles for therapeutic gene delivery and method for preparing the same are disclosed in Korea Patent Publication No. 10-2009-0097582, which relates to a gene medicine carrier which has improved biocompatibility and stability by cross-linking chitosan to alginate. In addition, the preparation method of bilayer scaffold in one-step and tissue regeneration method of bilayer scaffold obtained thereby are disclosed in Korea Patent Registration No. 10-1333381, but relates to a method of preparing a scaffold by cross-linking biocompatibility materials such as gelatin and polyvinyl alcohol with EDC.

Thus, in the patent documents as described above, there is no known cell carrier for skin tissue regeneration in which chitooligosaccharide (COS) having different molecular weights (kD) from each other is cross-linked to fish-derived collagen (Fish collagen, FC) and alginate (A) scaffold to improve the biocompatibility of fibroblasts.

DISCLOSURE

Technical Problem

Therefore, an object of the present invention is to provide a cell carrier and a method of preparing the same, having excellent biocompatibility by cross-linking chitooligosaccharide (COS) having different low molecular weights from each other to fish-derived collagen and alginate (FCA) scaffold.

Technical Solution

An object of the present invention is achieved by the step of comparing and analyzing the physical and chemical properties of the cell carrier for skin tissue regeneration (FCA/COS1) of the present invention, which includes the steps of (a) dissolving fish-derived collagen (FC) and alginate (A) in 0.02 M acetic acid to prepare collagen-alginate (FCA) solution in a weight ratio (w/w) of 70:30; (b) freeze-drying the FCA solution obtained in step (a) to prepare a collagen-alginate (FCA) scaffold; (c) immersing the FCA scaffold obtained in step (b) in a cross-linker solution for 3 to 5 hours to crosslink the same; (d) adding 1 to 3 kDa chitooligosaccharide (COS1) in an amount of 0.5 to 5% (w/w) with respect to the total weight of the cross-linker solution and cross-linking the same for 20 to 30 hours while the FCA scaffold of step (c) is immersed in the cross-linker solution; and (e) immersing the FCA/COS1 cell carrier obtained in step (d) in distilled water for 48 hours, washing the cell carrier, and then freeze-drying the cell carrier.

Advantageous Effects

The cell carrier of the present invention includes fish-derived collagen (FC), alginate (A), and chitooligosaccharide having low molecular weight of 1 to 3 kDa (COS1) so that the biocompatibility of dermal fibroblasts is significant, and it has an excellent effect of utilizing it as a cell carrier for skin tissue regeneration.

DESCRIPTION OF DRAWINGS

FIGS. 2a-2j illustrate scanning electron microscope (SEM) images of the surfaces of cell carriers prepared in Experimental Example 1 and Comparative Examples 1 to 4 according to the present invention.

FIGS. 9a-9j are images illustrating fluorescence analysis of cell viability of normal human dermal fibroblasts (NHDF)-neo cells cultured in cell carriers prepared in Experimental Example 1 and Comparative Examples 1 to 4 according to the present invention.

MODES OF THE INVENTION

The cell carrier for skin tissue regeneration of present invention includes fish-derived collagen (fish collagen, FC), alginate (A), and 1 to 3 kDa chitooligosaccharide (COS1).

According to the present invention, the chitooligosaccharide having different molecular weights (kDa) from each other were cross-linked to the fish-derived collagen and alginate scaffold to prepare cell carriers of Example 1 and Comparative Examples 2 to 4. Specifically, when the molecular weight of chitooligosaccharide is 1 to 3 kDa, 3 to 5 kDa, 5 to 10 kDa, and 10 kDa or more, respectively, it is referred to as FCA-COS1 (Example 1), FCA-COS2 (Comparative Example 2), FCA-COS3 (Comparative Example 3), and FCA-COS4 (Comparative Example 4).

The present invention cell carrier for skin tissue regeneration (FCA-COS1) is prepared by the steps of:

(a) dissolving fish-derived collagen and alginate in 0.02 M acetic acid to prepare collagen-alginate (FCA) solution in a weight ratio (w/w) of 70:30;

(b) freeze-drying the FCA solution obtained in step (a) to prepare a collagen-alginate (FCA) scaffold;

(c) immersing the FCA scaffold obtained in step (b) in a cross-linker solution for 3 to 5 hours to cross-link the same;

(d) adding 1 to 3 kDa chitooligosaccharide (COS1) in an amount of 0.5 to 5% (w/w) with respect to the total weight of the cross-linker solution and cross-linking the same for 20 to 30 hours while the FCA scaffold of step (c) is immersed in the cross-linker solution; and (e) immersing the FCA/COS1 cell carrier obtained in step (d) in distilled water for 48 hours, washing the cell carrier, and then freeze-drying the cell carrier.

According to the present invention, in step (a), one or more of distilled water and 0.02 M acetic acid are used as the solvent. The method of mixing the same is performed using a homogenizer and a magnetic stirrer so that the fish-derived collagen and alginate are most preferably soluble completely in the solvent, but the method of mixing the solvent is not limited thereto unless departing from the object of the present invention.

Further, the FCA solution prepared in step (a) may be used immediately in step (b), but it is most preferably centrifuged at 3000 rpm for 10 to 15 minutes to remove the bubble of the FCA solution to use the solution in step (b).

Figure 1A:
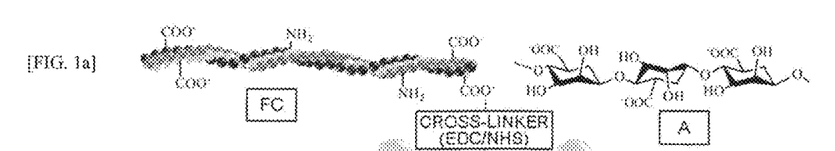
FIGS. 1a-1c are diagrams illustrating a molecular bond of a cell carrier prepared according to the present invention.
Figure 1B:
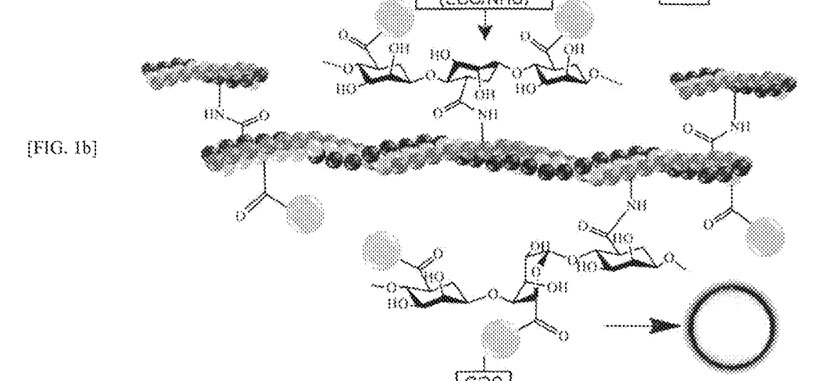

For the cross-linker of step (c), a condensing agent which active-esterifies the carboxyl group (COOH) of the FCA scaffold to semi-stable NHS-ester is dissolved in the solvent to use the same as a cross-linker solvent as illustrated in FIGS. 1(A) and (B). The cross-linker may be used one or an appropriate combination selected from the group consisting of N,N'-carbonyldiimidazole (CDI), N,N'-dicyclohexylcarbonylimide (DCC), N-ethoxycarbonyl-2-ethoxy-1,2-dihydroquinoline (EEDQ), 4-(4,6-dimethoxy-1,3,5-triazine)-4-methylmorpholium (DMT-MM), 2-benzotriazole-1,1,3,3-tetramethyluronium tetrafluoroborate (TBTU), 3,4-dihydro-3-hydroxy-4-oxo-1,2,3-benzotriazine (HODhbt), benzotriazol-1-oxy-tris-pyrrolidone-phosphonium hexafluorophosphate (PyBOP), benzotriazol-1-yl-oxy-tris-dimethylamino-phosphonium hexafluorophosphate (BOP), 1-ethyl-3-(3-dimethylaminopropyl) carbodiimide (EDC), N-hydroxysuccinimide (NHS), or the like. However, according to the present invention, it is most preferable to use a cross-linker solution in which EDC or NHS is solely used or properly combined and dissolved in an MES buffer.

Figure 1C:
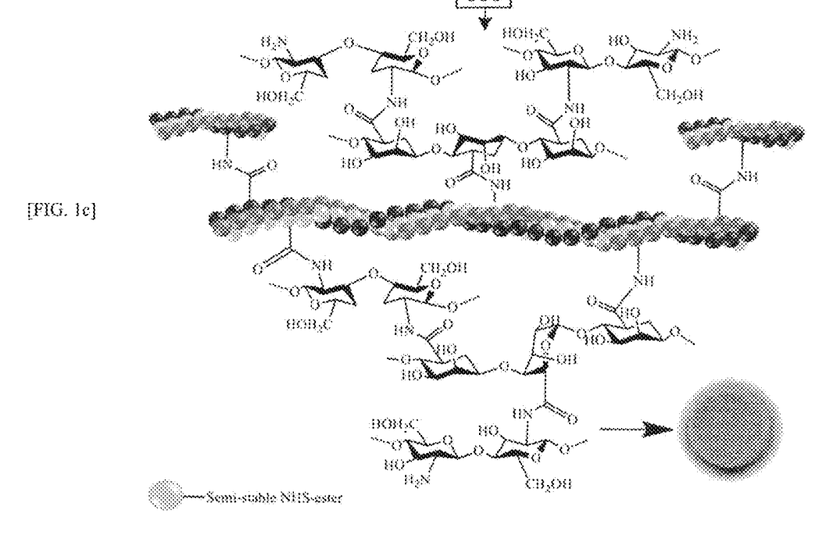

The chitooligosaccharide (COS1) of step (d) is cross-linked with the semi-stable NHS-ester prepared in the FCA scaffold prepared in step (c) to form FCA-COS1 scaffold as illustrated in FIG. 1(C).

Further, the addition amount of chitooligosaccharide in step (d) is 0.5 to 5% (w/w) and most preferably 1% (w/w) with respect to the amount of the cross-linker.

The cell carrier for skin tissue regeneration of the present invention may be used for regenerating skin tissue in which one or more kinds selected from the group consisting of a fibroblast, a skin cell, an angiogenic endothelial cell, and a stem cell are cultured to insert into a skin or used for preparing of an artificial skin in which the cells are proliferated in vitro to prepare an artificial skin.

The term "purpose of skin tissue regeneration" refers to the purpose of promoting skin tissue regeneration in aged skin, burn, wound, ulcer, or contusion skin, or for cosmetic care or plastic surgery.

The cell carrier for skin tissue regeneration of present invention further includes various physiologically active substances. The physiologically active substance is not particularly limited but may be any one that does not adversely affect cell adhesion and proliferation in the cell carrier. Specific examples thereof include a cell carrier to which one or more kinds selected from the group consisting of an antibiotic, an antiviral agent, an antibacterial agent, a nucleic acid, a peptide, and a protein are added. The antibiotic, antiviral agent, antibacterial agent, and the like are purposed to prevent infection of structures or regenerated skin tissues. The protein is one selected from the group consisting of a hormone, a cytokine, an enzyme, an antibody, a growth factor, a transcription factor, a vaccine, a structural protein, a ligand protein, a receptor, a cell surface antigen, and a receptor antagonist.

Unless defined otherwise, all technical and scientific terms used in the specification have the same meaning as commonly understood by one of skill in the art. Various science dictionaries containing terms used in the specification are well known and available in the art. The expression of the singular number in the specification includes the meaning of the plural number unless the meaning of the singular number is definitely different from that of the plural number in the context. The term "or" used in the specification refers to "and/or." Further, the term "including" is not closed-ended as well as other types such as "having," "consisting," and "comprising."

Hereinafter, specific contents of the present invention will be described in detail with reference to examples and production examples. The following examples are only for the description, and the present invention is not limited thereto.

The disclosure material used in the present invention is as follows. The fish-derived collagen (Fish collagen, FC) was extracted from the skin of *Paralichtys olivaceus* in the southern sea of Korea by Singh's method (Singh et al., Isolation and characterization of collagen extracted from the skin of striped catfish (Pangasianodon hypophthalmus) Food Chemistry, 124 (1), 97-105). The alginate (A), 1-ethyl-3-(3-dimethylaminopropyl) carbodiimide (EDC), N-hydroxysuccinimide (NHS), and 2-morpholinoethanesulfonic acid (MES) were purchased from Sigma-Aldrich Co. The chitooligosaccharide (COS) having 1 to 3 kDa, 3 to 5 kDa, 5 to 10 kDa, and 10 kDa or more was purchased from Kitto Life Co.

Example 1 (FCA-COS1): Preparation of a Cell Carrier for Skin Tissue Regeneration Using 1 to 3 kDa Chitooligosaccharide of the Present Invention The cell carrier for skin tissue regeneration of the present invention was prepared using the following method by cross-linking 1 to 3 kDa chitooligosaccharide (COS1) to collagen-alginate (FCA) scaffold.

Step 1: Collagen-alginate (FCA) scaffold (a) The fish-derived collagen was put in 0.02 M acetic acid at a concentration of 0.8% (w/v), dissolved at 4° C., and neutralized with 2 M NaOH to prepare 0.8% (w/v) collagen solution.

(b) Separately, the alginate was put in distilled water at a concentration of 3% (w/v) and dissolved at 60° C. to prepare 3% (w/v) alginate solution.

(c) The 0.8% (w/v) collagen solution prepared in step (a) and 3% (w/v) alginate solution prepared in step (b) were mixed in a weight ratio (w/w) of 70:30, stirred by a homogenizer for 5 minutes, and stirred by a magnetic stirrer for 24 hours, thereby preparing a collagen-alginate (FCA) solution.

(d) Next, to remove the bubbles of the FCA solution, the centrifugation was carried out at 3000 rpm for 15 minutes, and then the resulting solution was dispensed into a cell culture plate and lyophilized to prepare FCA scaffold.

(e) The FCA scaffold prepared as described above was first buffered in a 50 mM MES buffer for 30 minutes and then immersed in an EDC/NHS solution (50 mM MES, 33 mM EDC, and 6 mM NHS) for 4 hours to result in the cross-linking reaction.

Step 2: Collagen-alginate-chitooligosaccharide cell carrier (FCA/COS1)

(f) 1 to 3 kDa chitooligosaccharide (COS) was added with a concentration of 1% (w/v) in the EDC/NHS solution in which the FCA scaffold of step (e) in Example 1 was immersed and cross-linked for 20 hours, thereby preparing FCA/COS1 scaffold.

(g) The FCA/COS1 scaffold was immersed in distilled water for 48 hours to wash impurities and then freeze-dried to prepare the FCA/COS1 cell carrier of the present invention.

Comparative Example 1 (FCA): Preparation of Alginate-Collagen Cell Carrier for Skin Tissue Regeneration The collagen-alginate (FCA) scaffold prepared in step 1 of Example 1 was immersed in distilled water for 48 hours to wash impurities and then freeze-dried to prepare a cell carrier.

Comparative Example 2 (FCA-COS2): Preparation of a Cell Carrier for Skin Tissue Regeneration Using 3 to 5 kDa Chitooligosaccharide The cell carrier was prepared in the same method as Example 1 except that 3 to 5 kDa chitooligosaccharide was used instead of 1 to 3 kDa chitooligosaccharide used in step 2-(f) of Example 1.

Comparative Example 3 (FCA-COS3): Preparation of a Cell Carrier for Skin Tissue Regeneration Using 5 to 10 kDa Chitooligosaccharide The cell carrier was prepared in the same method as Example 1 except that 5 to 10 kDa chitooligosaccharide was used instead of 1 to 3 kDa chitooligosaccharide used in step 2-(f) of Example 1.

Comparative Example 4 (FCA-COS4): Preparation of a Cell Carrier for Skin Tissue Regeneration Using 10 kDa or More Chitooligosaccharide The cell carrier was prepared in the same method as Example 1 except that 10 kDa or more chitooligosaccharide was used instead of 1 to 3 kDa chitooligosaccharide used in step 2-(f) of Example 1.

Experimental Example 1: Morphological and Physicochemical Analysis of the Cell Carrier of the Present Invention SEM observation, porosity measurement, tensile strength measurement, and FTIR analysis were performed for the morphological and physicochemical analysis of the cell carrier of the present invention.

Morphology Analysis

Each surface of the cell carrier of the present invention prepared in Example 1 and the cell carriers in Comparative Examples 1 to 4 was photographed using a scanning electron microscope (SEM, Hitachi S-2700, 5.0 kV) at a low magnification (×200) and a high magnification (×500), and the pore sizes of the cell carriers were measured with an image analysis software (ImageJ Wayne, Rsband).

Figures 2, 2A, 2J:
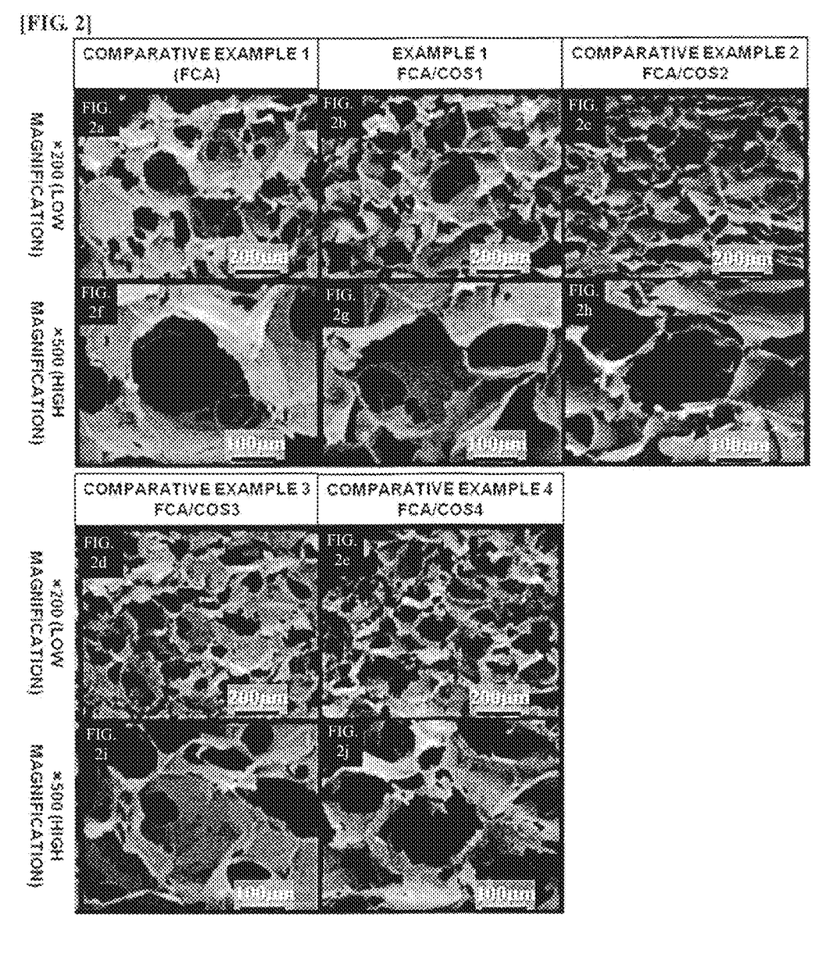

As illustrated in FIG. 2, when comparing the images for morphology of cell carriers taken with a scanning electron microscope, FCA-COS cell carriers of Example 1 and Comparative Examples 2 to 4 in which chitooligosaccharide was cross-linked have small pore sizes and no morphological change compared to FCA cell carrier of Comparative Example 1

Figure 3:
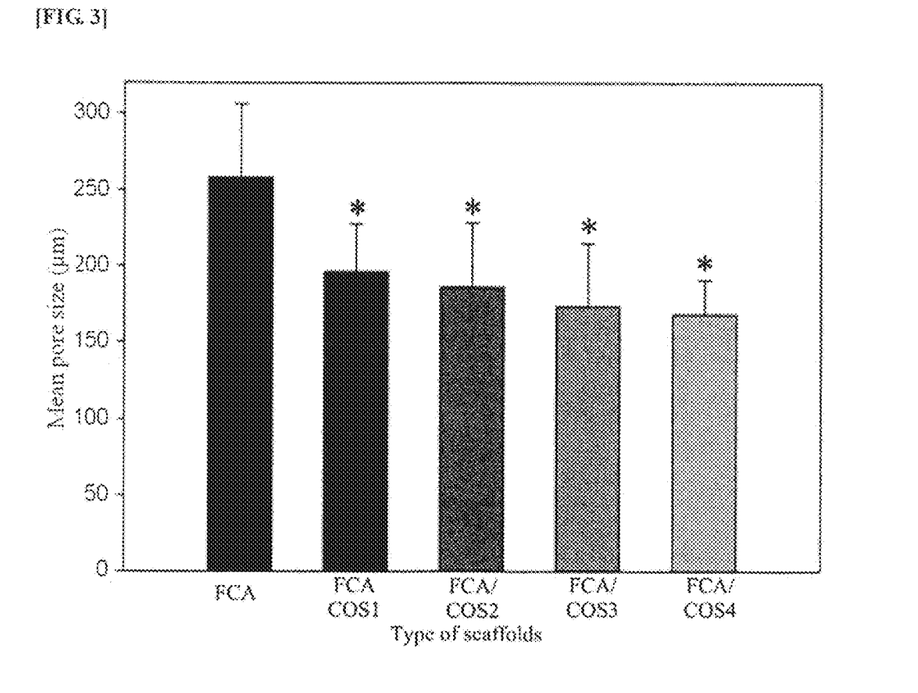
FIG. 3 is a graph illustrating average pore sizes of cell carriers prepared in Experimental Example 1 and Comparative Examples 1 to 4 according to the present invention.

Further, as illustrated in FIG. 3, the pore size of each FCA-COS cell carrier in Example 1 and Comparative Examples 2 to 4 was exhibited to be 168±22 μm to 196±31 μm, and the pore size of the FCA cell carrier in Comparative Example 1 was exhibited to be 258±47 μm. 168±22 μm to 196±31 μm, the pore size of FCA-COS cell carrier according to the present invention, corresponds to 100 to 200 μm which is the ideal pore size for a cell carrier for skin tissue regeneration (Wang, X et al. The roles of knitted mesh-reinforced collagen-chitosan hybrid scaffold in the one-step repair of full-thickness skin defects in rats. Acta biomaterialia, 9(8), 7822-7832, 2013).

Measurement of Porosity and Tensile Strength

The porosity of the FCA-COS cell carriers prepared in Example 1 and Comparative Examples 2 to 4 and the cell carrier in Comparative Example 1 was measured by an ethanol permeation experiment (Tan et al., 2009), and the tensile strength thereof was measured using a universal tensile machine (Top-tech 2000, Chemilab).

In the experimental method for porosity, the weight (W0) of the cell carrier was first measured, and the cell carrier was immersed in 100% ethanol at room temperature for 15 minutes. After 15 minutes, the cell carrier was removed from the ethanol, the ethanol was removed from the surface thereof, and then the weight (W1) of the cell carrier was measured. The measured W0 and W1 were substituted into the following Formula 1 to prepare the porosity. P is the specific gravity of ethanol (0.789 mg/ml), and Vs is the geometrical volume of the cell carrier.

Formula 1

Porosity (%)=(W1−W0)/pVs×100    [Equation 1]

Figure 4:
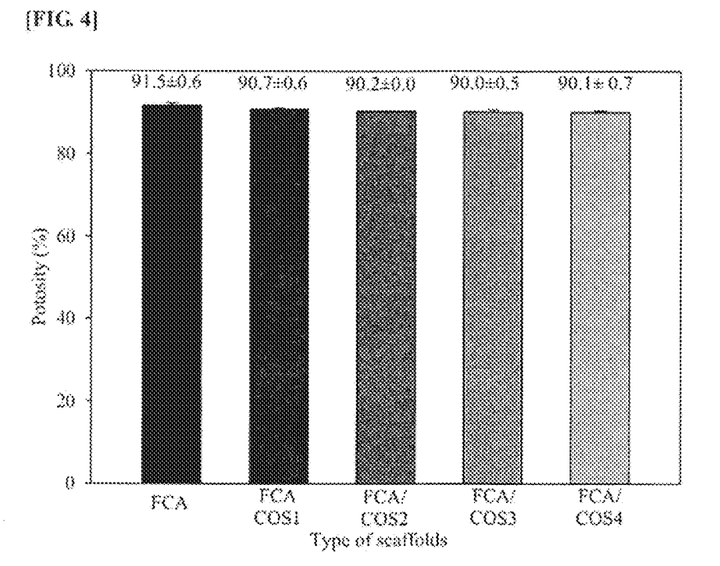
FIG. 4 is a graph illustrating the average porosity of cell carriers prepared in Experimental Example 1 and Comparative Examples 1 to 4 according to the present invention.

As illustrated in FIG. 4, the porosity of the FCA-COS cell carriers prepared according to Example 1 and Comparative Examples 2 to 4 and the FCA cell carrier of Comparative Example 1 exhibited porosity of 90% or more.

Figure 5:
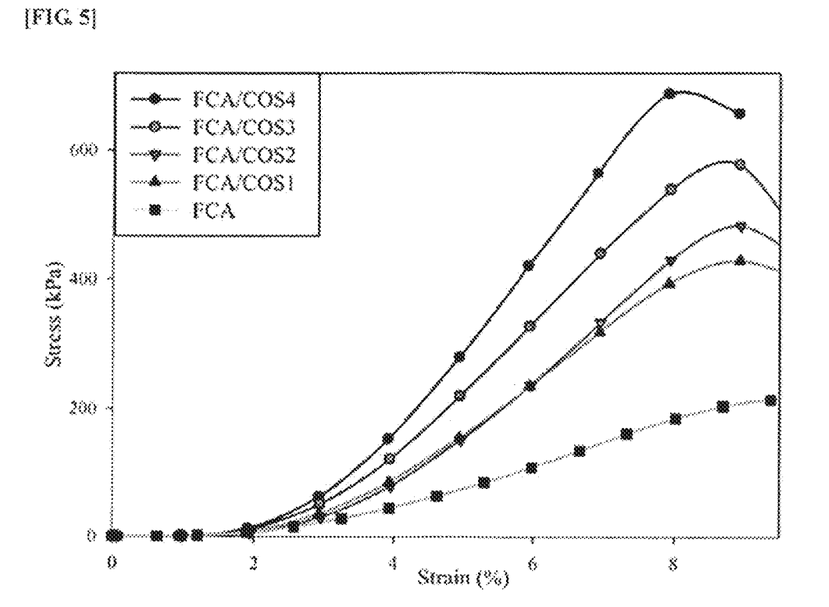
FIG. 5 is a graph illustrating average tensile strengths of cell carriers prepared in Experimental Example 1 and Comparative Examples 1 to 4 according to the present invention.

As illustrated in FIG. 5, the tensile strength of the cell carrier of Comparative Example 1 was 2.57±0.2 MPa, the tensile strength of the cell carriers of Example 1 and Comparative Examples 2 to 4, respectively, were 7.17±0.7 MPa, 8.79±0.2 MPa, 8.51±0.2 MPa, and 11.31±1 MPa, indicating that the tensile strength of the FCA scaffold was increased when COS was cross-linked to the FCA scaffold.

Total Reflection Measurement Fourier Transform Infrared Spectroscopy Analysis

Total reflection Fourier transform infrared spectroscopy (FTIR, ALPHA, Bruker optics, 400-4000 nm) was performed in order to physiochemically analyze the cross-linking morphology of the cell carriers prepared according to Example 1 and Comparative Examples 2 to 4.

Figure 6:
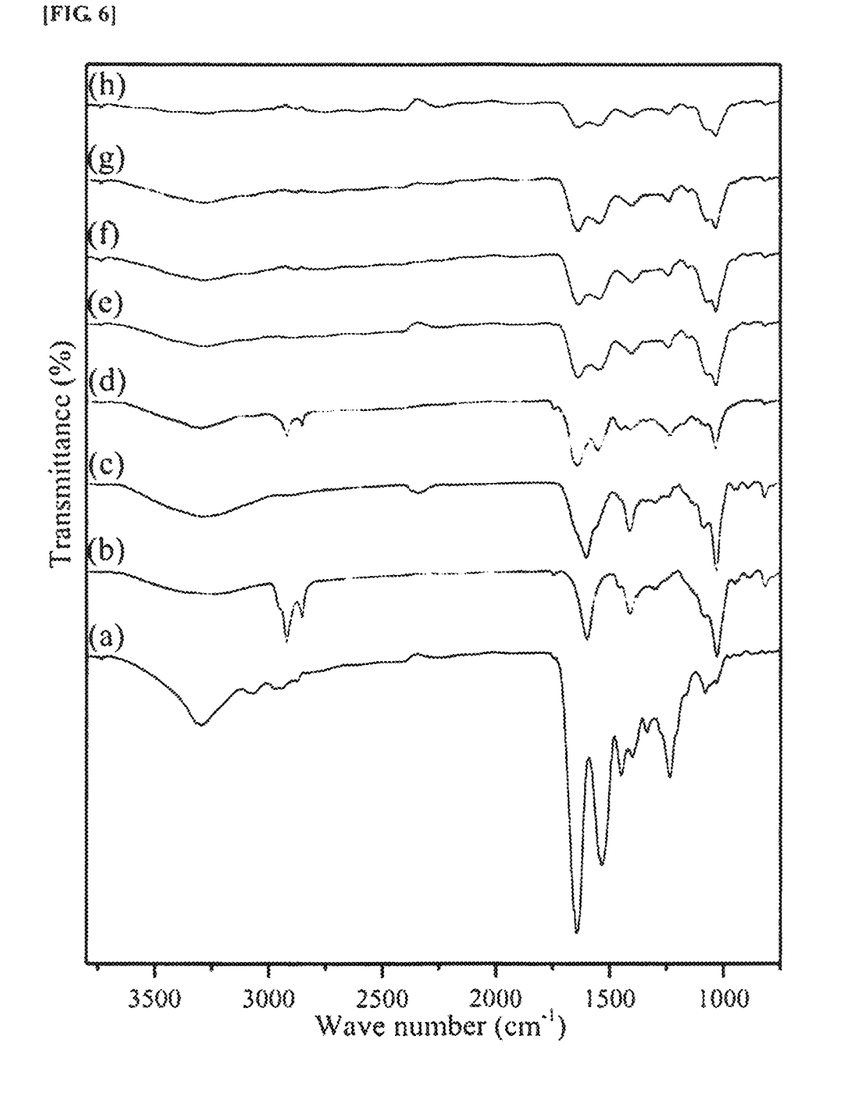
FIG. 6 is a graph illustrating the surface analysis of cell carriers prepared in Experimental Example 1 and Comparative Examples 1 to 4 according to the present invention using Fourier-transform infrared spectroscopy (FTIR).

As illustrated in FIG. 6 and Table 1 as described below, the five major peaks of the collagen extracted from fish skin were first confirmed to be amide A ($\sim$3299 $cm^{-1}$), amide B ($\sim$3074 $cm^{-1}$), amide I ($\sim$1647 $cm^{-1}$), amide II ($\sim$1534 $cm^{-1}$), and amide III ($\sim$1234 $cm^{-1}$). Such confirmation indicates that the collagen was successfully extracted from the fish skin. The major peaks of the alginate were observed to be the asymmetric and symmetrical stretching vibration peaks of the carboxylate salt group at $\sim$1599 $cm^{-1}$ and $\sim$1408 $cm^{-1}$ and the stretching peaks of C—O—C of the glycosidic bond at $\sim$1035 $cm^{-1}$. As a result of observing peaks of the crosslinked FCA scaffold by infrared spectroscopic analysis, it was confirmed that the amide bond formed by the carbodiimide reaction did not affect the structural changes of collagen and alginate. The reduction of the peak at a wavenumber of 3650 to 3300 $cm^{-1}$ contributes to the removal of a hydrogen bond from FC-FC and FC-A by EDC cross-linking. The peaks obtained after cross-linking COS with four different molecular weights having IR peaks similar to those of chitosan were confirmed that IR peaks corresponding to the bond of amide A and O—H were reduced. Such results indicate that the hydrogen bond due to the increase of the molecular weight of COS is removed from the cell carrier.

TABLE 1

| Types of fabrication | Absorption band peaks ($cm^{-1}$) | | | | | |
|---|---|---|---|---|---|---|
| | Amide A | Amide B | Amide I | Amide II | Amide III | C—O—C |
| FC | 3299 | 3074 | 1647 | 1534 | 1234 | — |
| SA | — | — | — | — | — | 1035 |
| FCA-NCL | 3285 | 3072 | 1602 | 1556 | 1238 | 1032 |
| FCA-CL | 3299 | 3076 | 1648 | 1550 | 1235 | 1035 |
| FCA/COS1 | 3295 | 3077 | 1636 | 1544 | 1238 | 1033 |
| FCA/COS2 | 3295 | 3075 | 1636 | 1548 | 1240 | 1030 |
| FCA/COS3 | 3294 | 3076 | 1637 | 1548 | 1240 | 1030 |
| FCA/COS4 | 3299 | 3089 | 1636 | 1546 | 1246 | 1035 |

NCL = non cross-linked,
CL = cross-linked by EDC

Experimental Example 2: Evaluation of Biocompatibility of the Cell Carrier of the Present Invention Biodegradation rate, MTT assay, fluorescence analysis, and cell adhesion ability were confirmed as follows in order to evaluate the biocompatibility of the cell carrier of the present invention.

Biodegradability

The biodegradability of the FCA-COS cell carriers prepared in Example 1 and Comparative Examples 2 to 4 and the FCA cell carrier of Comparative Example 1 was confirmed by the in vitro enzymatic degradation method (Choi et al., 1999). In the experiment, the cell carriers were weighed (W0) and immersed in a PBS solution containing 125 units (125 CDU) of collagenase (type 1 collagenase from *Clostridium histolyticum*) at 37° C. for 12 days. The immersed cell carriers were taken out from the PBS solution at intervals of 2 days, washed with distilled water and then freeze-dried. Then, the weight (W1) of the freeze-dried cell carrier was measured. The biodegradability was calculated by substituting W0 and W1 measured as described above into the following Formula 2.

Biodegradability (%)=(W1−W0)/W0×100    [Equation 2]

Figure 7:
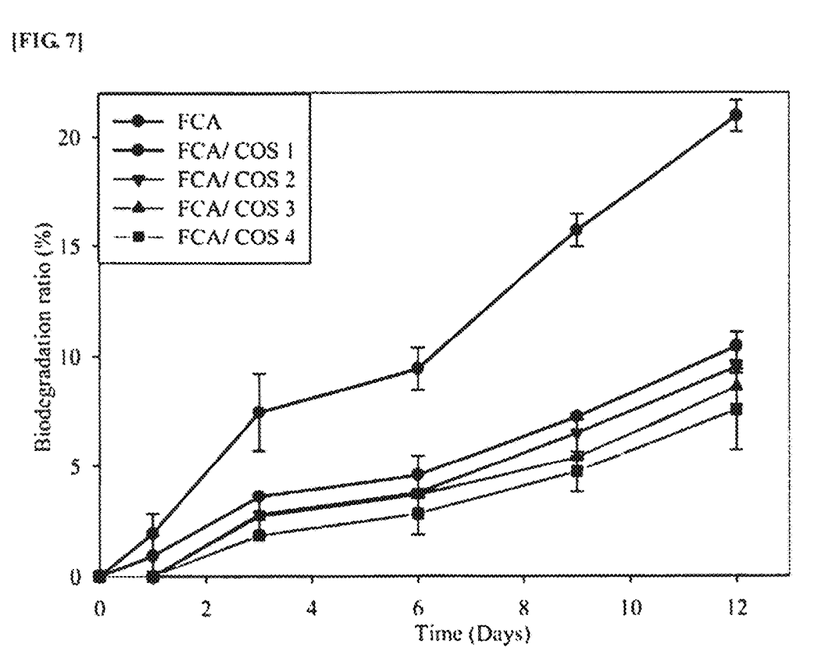
FIG. 7 is a graph illustrating the biodegradability of cell carriers prepared in Experimental Example 1 and Comparative Examples 1 to 4 according to the present invention.

As illustrated in FIG. 7, the biodegradability of the cell carrier reacted with collagenase for 12 hours was 21% in Comparative Example 1 and 10.5%, 9.5%, 8.6%, and 7.6% in Example 1 and Comparative Examples 2 to 4, respectively. These results confirmed that the FCA-COS cell carrier can stay for a long time in vivo with a collagenase enzyme than the FCA cell carrier, thereby maintain the cell carrier stable.

Cell Culture

NHDF-neo cell (ATCC, PCS-201-010), a human skin fibroblast cell, was used to confirm cell viability and proliferation rate of a cell carrier for skin tissue regeneration of the present invention. DMEM supplemented with 10% FBS and 1% penicillin/streptomycin was used as the cell culture medium of NHDF-neo cell. The culture conditions were 37° C. and 5% $CO_2$, and cell culture medium and medium condition in which NHDF-neo cell was dispensed also were the same as described above.

In order to dispense the NHDF-neo cell on each cell carrier, UV-irradiated and sterilized cell carriers were buffered in the culture medium for 24 hours. Then, NHDF-neo cell cultured at a confluency of 80 to 85% in a plate whose area size is the same as one of the cell carrier was suspended to the culture medium, and the resultant product was dispersed on the cell carrier. The result was used in the following experiments to determine cell viability of the cell carrier for skin tissue regeneration of the present invention.

MTT Assay

Each cell carrier in which the NHDF-neo cell was dispensed was cultured for 2, 5, 7, and 12 days and then washed with PBS. Then, the cell carrier was cultured in a cell culture medium supplemented with 0.5 mg/ml MTT for 4 hours to induce a reduction reaction. After the reaction, the medium was carefully removed, and DMSO solution was added to dissolve the MTT formazan formed by the reduction reaction. Then, centrifugation was performed at 4000 rpm for 5 minutes to recover only supernatant. The supernatant was used as a sample for measuring the absorbance at a wavelength 540 nm using ELISA microplate reader (Gen5 ELISA BioTek, USA). The cell viability was quantified as a percentage (%) of absorbance of the cell carrier of each experimental group versus the absorbance of the FCA cell carrier of Comparative Example 1 at 0 hour.

Figure 8:
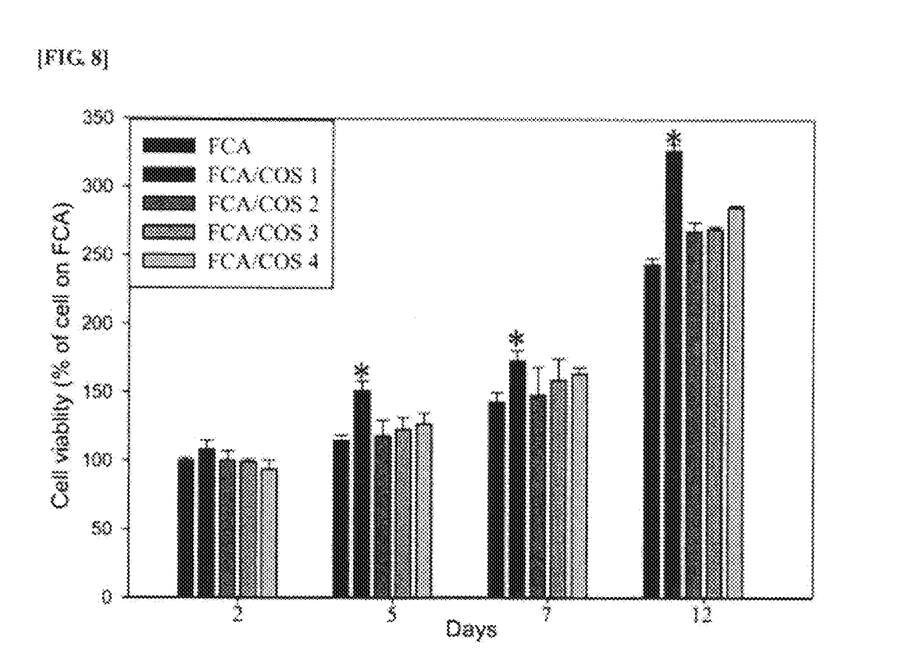
FIG. 8 is a graph illustrating results of 3-(4,5-dimethylthiazol-2-yl)-2,5-diphenyltetrazolium bromide (MTT) assay of NHDF-neo cells cultured in cell carriers prepared in Experimental Example 1 and Comparative Examples 1 to 4 according to the present invention.

As illustrated in FIG. 8, in the cell viability of NHDF-neo cell proliferated on each cell carrier after cultured for 12 hours, those of the FCA-COS cell carriers of Example 1 and Comparative Examples 2 to 4 were higher than that of the FCA cell carrier of Comparative Example 1. In particular, the FCA-COS1 of Example 1 prepared with 1 to 3 kDa COS of the present invention exhibited the cell viability of 173±7% higher than those of the other cell carriers.

Fluorescence Analysis

In order to confirm the cell proliferation rate, FDA was used, which is a fluorescent substance stained in living cells and glows a fluorescent. The FDA is de-acetylated by the intracellular esterase activity of living cells to glow a fluorescent. First, the respective cell carriers in which NHDF-neo cells were dispersed were cultured for 1 day and 12 days, and then washed with PBS. The cell carriers were then stained for 15 min in PBS supplemented with 5 µg/ml FDA, then washed with PBS. Then, the NHDF-neo cells were observed using a fluorescence microscope (Leica DMI3000B).

Figures 9, 9A, 9J:
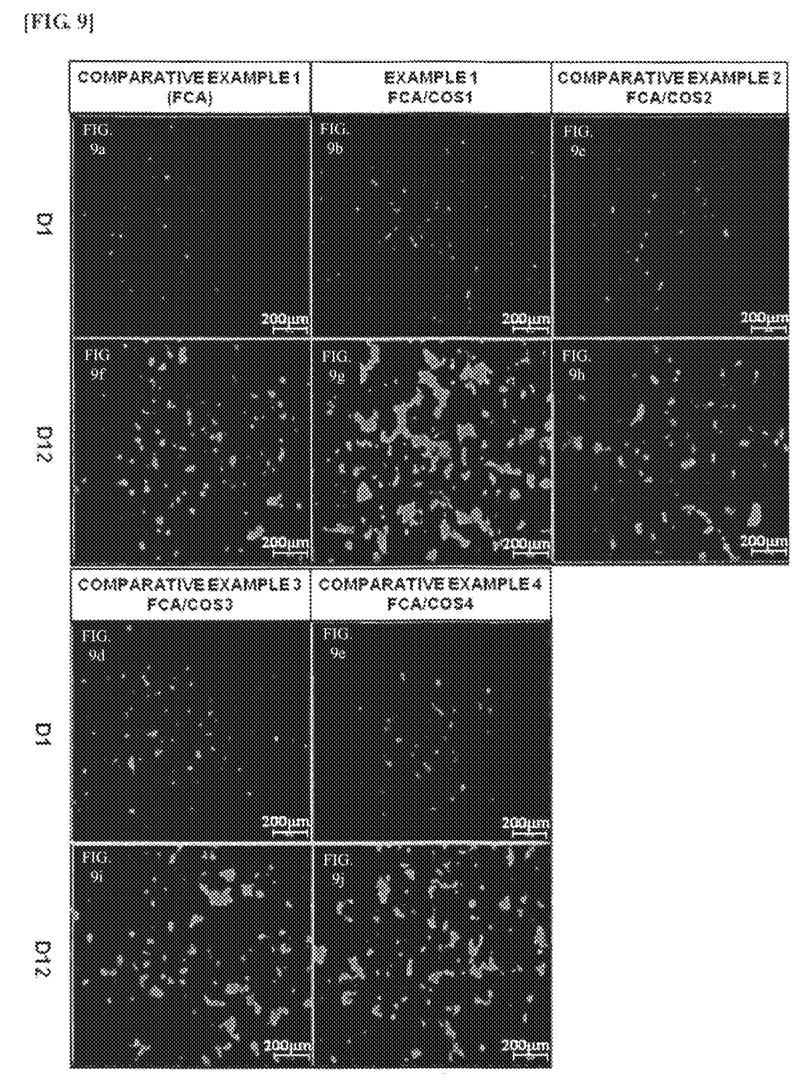

As illustrated in FIG. 9, for the fluorescence intensity of the NHDF-neo cell after 12 days of culturing, those of the FCA-COS cell carriers of Example 1 and Comparative Examples 2 to 4 was higher than that of the FCA cell carrier of Comparative Example 1. In particular, the FCA-COS1 of Example 1 including 1 to 3 kDa COS of the present invention had high fluorescence intensity compared to than those of the other cell carriers.

Observation of Cell Adhesion Ability

The cell adhesion ability of NHDF-neo cells for the FCA-COS cell carrier of Example 1 and the FCA cell carrier of Comparative Example 1 was confirmed using a scanning electron microscope (SEM, Hitachi S-2700, 5.0 kV).

Figure 10:
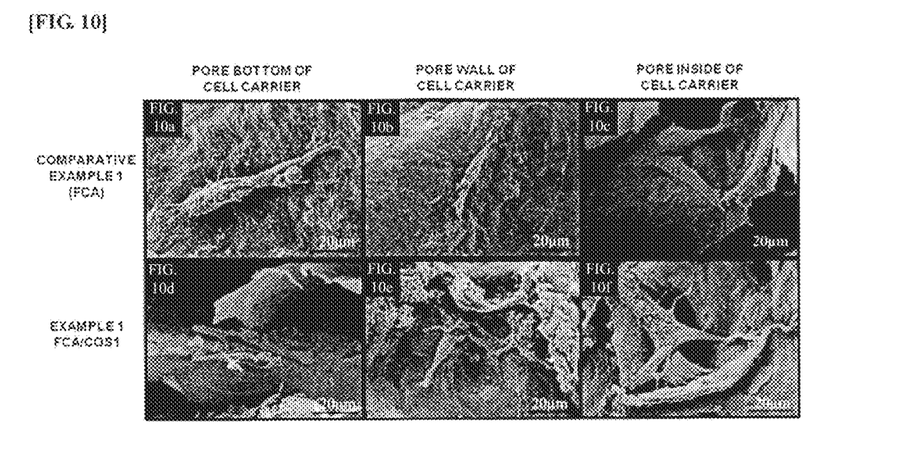
FIGS. 10a-10f are images illustrating the cell adhesion ability of NHDF-neo cells cultured in cell carriers prepared in Experimental Example 1 and Comparative Examples 1 to 4 according to the present invention, which is confirmed through a scanning electron microscope.

As illustrated in FIG. 10, after 7 days of culturing, NHDF-neo cells were flatly adhered at the bottom (d) and the wall (e) of the pores of the FCA-COS cell carrier of Example 1 of the present invention and were well adhered in the pores (f) with extending pseudopods. Relatively, such adhesion was not confirmed in the FCA cell carrier of Comparative Example 1.

INDUSTRIAL APPLICABILITY

As described above, the cell carrier of the present invention includes fish-derived collagen (Fish collagen, FC), alginate (A), and 1 to 3 kDa chitooligosaccharide (COS). Thus, it is a very useful invention in the medical biomaterial industry due to its excellent biocompatibility when used as a cell carrier for human skin tissue regeneration.

The invention claimed is:

1. A method of preparing a collagen-alginate-chitooligosaccharide cell carrier for skin tissue regeneration, the method comprising the steps of:
    (a) dissolving fish-derived collagen and alginate in 0.02 M acetic acid to prepare collagen-alginate (FCA) solution in a weight ratio (w/w) of 70:30;
    (b) freeze-drying the FCA solution obtained in step (a) to prepare a collagen-alginate (FCA) scaffold;
    (c) immersing the FCA scaffold obtained in step (b) in a cross-linker solution for 3 to 5 hours to cross-link the same;
    (d) adding 1 to 3 kDa chitooligosaccharide (COS1) in an amount of 0.5 to 5% (w/w) with respect to the total weight of the cross-linker solution and cross-linking the same for 20 to 30 hours while the FCA scaffold of step (c) is immersed in the cross-linker solution; and
    (e) immersing the FCA/COS1 cell carrier obtained in step (d) in distilled water for 48 hours, washing the cell carrier, and then freeze-drying the cell carrier,
    wherein the cross-linker in step (c) is one or more selected from the group consisting of N,N'-carbonyldiimidazole (CDI), N,N'-dicyclohexylcarbonylimide (DCC), N-ethoxycarbonyl-2-ethoxy-1,2-dihydroquinoline (EEDQ), 4-(4,6-dimethoxy-1,3,5-triazine)-4-methylmorpholium (DMT-MM), 2-benzotriazole-1,1,3,3-tetramethyluronium tetrafluoroborate (TBTU), 3,4-dihydro-3-hydroxy-4-oxo-1,2,3-benzotriazine (HODhbt), benzotriazol-1-oxy-tris-pyrrolidone-phosphonium hexafluorophosphate (PyBOP), benzotriazol-1-yl-oxy-tris-dimethylamino-phosphonium hexafluorophosphate (BOP), 1-ethyl-3-(3-dimethylaminopropyl) carbodiimide (EDC), and N-hydroxysuccinimide (NHS).

2. A collagen-alginate-chitooligosaccharide cell carrier for skin tissue regeneration prepared according to the method of claim 1.

* * * * *